United States Patent
Nicolas et al.

(10) Patent No.: US 11,826,612 B2
(45) Date of Patent: Nov. 28, 2023

(54) PORTABLE INSTRUMENT FOR MANAGING A SPORTS OR WELL-BEING ACTIVITY

(71) Applicant: The Swatch Group Research and Development Ltd, Marin (CH)

(72) Inventors: Cedric Nicolas, Neuchatel (CH); Kamiar Aminian, La Tour-de-Peilz (CH); Joaquin Cabeza De Pablo, Renens (CH); Martin Savary, Yverdon-les-Bains (CH); Abolfazl Soltani, Lausanne (CH); Hooman Dejnabadi, Orbe (CH)

(73) Assignee: The Swatch Group Research and Development Ltd, Marin (CH)

( * ) Notice: Subject to any disclaimer, the term of this patent is extended or adjusted under 35 U.S.C. 154(b) by 488 days.

(21) Appl. No.: 16/874,745

(22) Filed: May 15, 2020

(65) Prior Publication Data
US 2021/0001175 A1    Jan. 7, 2021

(30) Foreign Application Priority Data
Jul. 1, 2019  (EP) ..................................... 19183638

(51) Int. Cl.
*A63B 24/00*    (2006.01)
*A61B 5/11*    (2006.01)
(Continued)

(52) U.S. Cl.
CPC ........ *A63B 24/0062* (2013.01); *A61B 5/1123* (2013.01); *A61B 5/681* (2013.01);
(Continued)

(58) Field of Classification Search
CPC ..... A61B 5/1123; A61B 5/681; G01C 22/006; G01P 1/02; G01P 13/00; G01S 19/47; G04G 21/02; A63B 24/0062
(Continued)

(56) References Cited

U.S. PATENT DOCUMENTS 6,532,432 B1    3/2003  Nagatsuma et al.
2013/0271314 A1    10/2013  Mole et al.
(Continued)

FOREIGN PATENT DOCUMENTS

JP    2018-205195 A    12/2018

OTHER PUBLICATIONS

Japanese Office Action dated May 25, 2021 in Japanese Patent Application No. 2020-098217 (with English translation), 12 pages.
(Continued)

*Primary Examiner* — Kesha Frisby
(74) *Attorney, Agent, or Firm* — Oblon, McClelland, Maier & Neustadt, L.L.P.

(57) ABSTRACT

A portable instrument provided with a device for controlling or managing a sports or well-being activity of a person wearing the portable instrument. The control device includes at least a motion sensor and a pressure sensor connected to a calculation unit, and a GNSS receiver module connected to the calculation unit. The calculation unit of the control device is arranged to activate the GNSS receiver module for a time of activation defined subsequent to variations in movement detected by the motion sensor differing from known movement data or walking profiles in order to determine at least one reference speed of the person, and to deactivate the GNSS receiver module after the activation time for a deactivation time greater than the activation time.

17 Claims, 6 Drawing Sheets

(51) Int. Cl.
  *A61B 5/00* (2006.01)
  *G01C 22/00* (2006.01)
  *G01P 1/02* (2006.01)
  *G01P 3/00* (2006.01)
  *G01P 13/00* (2006.01)
  *G01S 19/47* (2010.01)
  *G04G 21/02* (2010.01)
  *A63B 69/00* (2006.01)

(52) U.S. Cl.
  CPC .............. *G01C 22/006* (2013.01); *G01P 1/02* (2013.01); *G01P 3/00* (2013.01); *G01P 13/00* (2013.01); *G01S 19/47* (2013.01); *G04G 21/02* (2013.01); *A63B 69/0028* (2013.01); *A63B 2220/17* (2013.01); *A63B 2220/40* (2013.01); *A63B 2220/73* (2013.01); *A63B 2220/74* (2013.01); *A63B 2220/836* (2013.01); *A63B 2220/89* (2013.01)

(58) Field of Classification Search
  USPC .......................................................... 702/142
  See application file for complete search history.

(56) References Cited

U.S. PATENT DOCUMENTS

2017/0242131 A1   8/2017   Mole et al.
2018/0356534 A1   12/2018  Sugiyama et al.
2019/0113365 A1*  4/2019   Afzal ....................... G01C 5/06

OTHER PUBLICATIONS

European Search Report dated Jan. 17, 2020 in European Application No. 19183638.6 filed on Jul. 1, 2019 (with English Translation of Categories of Cited Documents), 4 pages.

* cited by examiner

PORTABLE INSTRUMENT FOR MANAGING A SPORTS OR WELL-BEING ACTIVITY

CROSS-REFERENCE TO RELATED APPLICATION

This application claims priority to European Patent Application No. 19183638.6 filed on Jul. 1, 2019, the entire disclosure of which is hereby incorporated herein by reference.

TECHNICAL FIELD OF THE INVENTION

The invention relates to a portable instrument, such as a watch, provided with a device for controlling or managing a sports or well-being activity of a person wearing the portable instrument during activity.

The invention also relates to a method for managing a sports or well-being activity via the operating portable instrument.

PRIOR ART

Walking speeds or gaits are among the most important parameters for characterising the daily mobility of people. For example in sports uses, speed can be used to evaluate athletes and thus prepare customised training sessions, with the goal of improving the performance of each athlete and reducing the risk of injuries. In medical uses, speed is used to evaluate the health of a person, with the goal of helping doctors in order to establish a diagnosis, predict and prevent numerous diseases, such as cardiovascular diseases or diabetes or excess weight.

A global navigation satellite system (GNSS) is a basic system widely used to measure for example the walking speed of a person. Such a GNSS system is precise and numerous portable instruments have been designed to integrate such a transponder, the measurements of which can be used to calculate the walking speed of a person even in real conditions. However, there are certain locations where the GNSS signal is weak or could even be lost because of the lack of satellite coverage, like inside tunnels, near tall buildings, in narrow valleys. Moreover, a GNSS transponder consumes a lot of electric energy. Therefore, it is preferable to use it sporadically rather than continuously to reduce the electricity consumption of the portable instrument that comprises it.

The patent application WO 2018/106319 A1 describes a portable instrument, such as a mobile phone or a smartwatch, for estimating in real time parameters of movement of a person, such as a speed or a walking or running pace. The instrument comprises a GNSS transponder with a Kalman filter for determining a first speed derived from the GNSS positions of the person, a second speed derived from the Doppler shifts of the GNSS signals and a number of observed steps of the user. The instrument further comprises units for detecting movement, which can provide a speed derived from the GNSS positions and a speed derived from the GNSS Doppler shifts. However, the use of the GNSS transponder of the instrument is used for long periods of time to determine a walking speed or pace of the person, which leads to high electricity consumption and constitutes a disadvantage.

The patent application WO 2012/045484 A1 describes a pedometer system calibrated by GPS. The system can be worn by a person, such as a sports watch. The system comprises a GNSS receiver designed to obtain the position and/or the speed of the person and a pedometer for counting the steps taken by the person. The data of the GNSS receiver is used to calibrate the pedometer each time that the user is determined to travel a distance greater than a predefined distance value over a period during which the signals obtained by the GNSS receiver are precise. Like for the previous document, the GNSS receiver of the instrument is used for long periods of time to determine a walking speed or pace of the person, which leads to high electricity consumption and constitutes a disadvantage.

The patent U.S. Pat. No. 7,245,254 B1 describes an electronic exercise device for controlling the activity or mobility of a person. The electronic device continuously calculates the steps of the user using a GPS circuit for determining the position and a computer instrument by executing a process of iterative calibration. The device thus comprises a GPS circuit, a pedometer, an accelerometer, a sensor for checking the pulse and a temperature sensor. When the GPS satellite signals are accessible, the GPS circuit corrects the accumulated error of the pedometer and/or of the accelerometer. Like for the previous documents, the GPS circuit of the instrument is used for long periods of time to continuously determine steps or physical parameters of the person, which leads to high electricity consumption and constitutes a disadvantage.

SUMMARY OF THE INVENTION

The goal of the invention is therefore to overcome the disadvantages mentioned above with a portable instrument provided with a device for controlling or managing a sports or well-being activity of a person wearing the portable instrument and by reducing the operating time of a GNSS receiver module of the device in order reduce the electricity consumption while precisely determining the daily mobility of the person by the device.

For this purpose, the invention relates to a portable instrument provided with a device for controlling or managing a sports or well-being activity of a person wearing the portable instrument, which comprises the features of independent claim 1.

Specific embodiments of the portable instrument are defined in dependent claims 2 to 9.

One advantage of the portable instrument provided with the control device lies in the fact that the GNSS receiver module is activated for short periods of time to determine changes in walking pace or profile of a person. This allows to reduce the electricity consumption of the control device while calibrating the control device of the portable instrument for the person using it over a long term. Thus, the control device learns the daily mobility profile of the person to have a customised and self-adaptive calibration by the calibration operation with the activation of the GNSS receiver module for short periods of time to precisely determine the speed data in particular.

Advantageously, before a new activation of the GNSS receiver module, a deactivation time must be exceeded independently of the reception of new walking or gait models or profiles. To do this, the activation time of the GNSS receiver module is approximately 5 times less than the deactivation time of the GNSS receiver module.

For this purpose, the invention also relates to a method for managing a sports or well-being activity of a person via the portable instrument, which comprises the features mentioned in independent claim 10.

Specific steps of the method for managing a sports or well-being activity of a person are defined in dependent claims 11 to 16.

BRIEF DESCRIPTION OF THE DRAWINGS

The goals, advantages and features of a portable instrument or of a method for managing a sports or well-being activity of a person will be clearer in the following description on the basis of at least one non-limiting embodiment illustrated by the drawings in which.

DETAILED DESCRIPTION OF THE INVENTION

In the following description, all the electronic components of a portable instrument, which is provided with a device for controlling a sports or well-being activity of a person wearing the portable instrument, which are well known to a person skilled in the art in this technical field, are only described in a simplified manner. It should be noted that it is desired to manage a sports or well-being activity of a person, that is to say a movement by foot. It must be understood that by only defining a walk or gait of the person, this also comprises a run for example.

Figure 1:
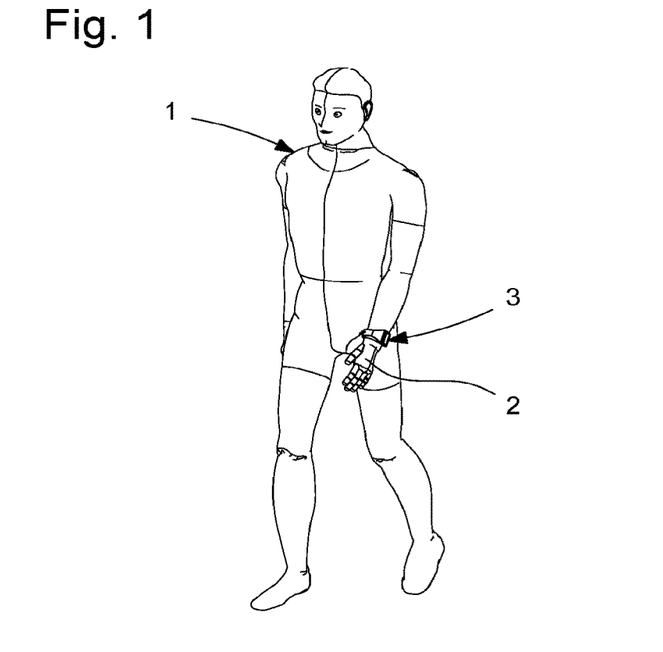
FIG. 1 is a perspective view of a person wearing the portable instrument in the form of a wristwatch according to the invention.
Figure 3:
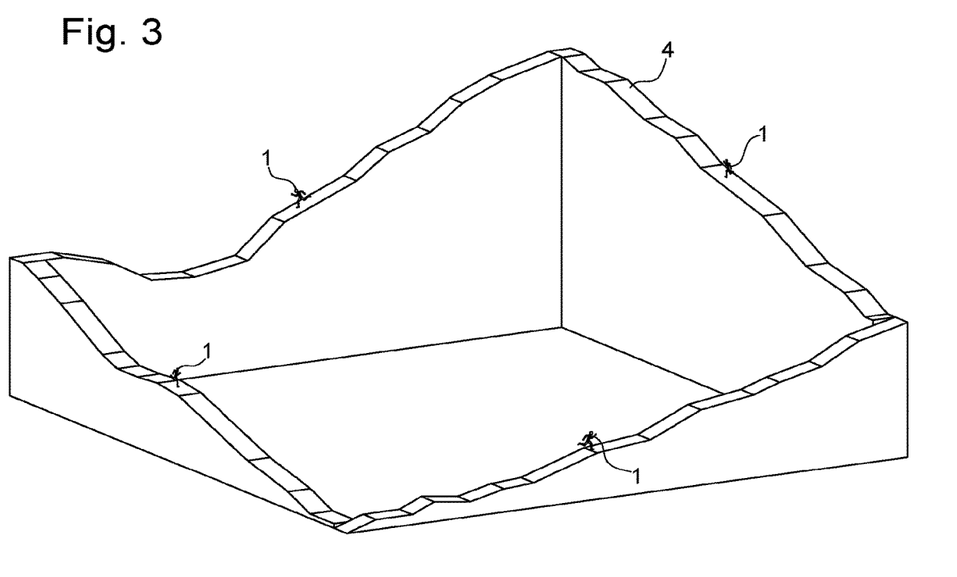
FIG. 3 is a perspective diagram of a path followed by a person provided with the portable instrument during a walk or a run.

FIG. 1 shows a person 1 in a standing position with the feet in contact with the ground. The person 1 wears a portable instrument 3, which is in this embodiment a wristwatch that the person wears on his left wrist 2 for example. The wristwatch 3 is provided with a device for controlling or managing a sports or well-being activity, explained below. The smartwatch 3 is configured by its control device to monitor the activity and deduce various parameters of the person 1 while said person moves on foot (that is to say by running or by walking) along a trajectory 4, the variations in altitude or in slope of which are voluntarily exaggerated as shown in FIG. 3. The control device comprises at least one motion sensor, which can be an accelerometer with one or two or preferably three axes of measurement, and also for example at least one pressure sensor, such as a barometer or altimeter for determining the altitude or the slope during a walk or run along a trajectory 4 or path in nature or in an urban area.

Figure 2:
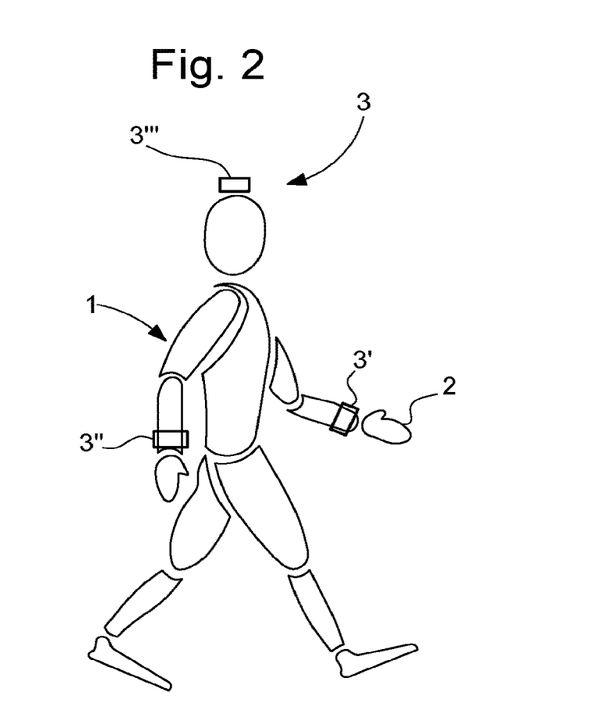
FIG. 2 shows a simplified view of a person wearing the portable instrument, which comprises according to an alternative embodiment three parts according to the invention.

In FIG. 2 according to an alternative embodiment, the person 1 wears a portable instrument 3, which can be composed of three parts 3', 3", 3'" not directly connected mechanically, but connected electrically or wirelessly. These three parts all comprise the components of the control device. In a first part 3' of the portable instrument 3, which is fastened for example to the left wrist 2 of the person 1 in the form of a bracelet or of a wristwatch, at least one first sensor of the control device is provided. This first part 3' can comprise a calculation unit for the processing of all the data or measurements of the three parts of the portable instrument 3. This first sensor can be a motion sensor with at least one accelerometer for example with three axes of measurement. The motion sensor can also be an inertial motion sensor with 9 axes having a triaxial accelerometer, a triaxial gyroscope and a triaxial magnetic sensor. In a second part 3" of the portable instrument 3, which is fastened for example to the right wrist of the person 1 in the form of a bracelet, at least one second sensor of the control device is provided. This second sensor can be a pressure sensor, such as an altimeter or barometer. Finally in a third part 3'" of the portable instrument 3, which is mounted on the head of the person 1 in a headband or a helmet, the GNSS receiver module is provided, which is used as a reference method.

It should be noted that the motion sensor can also be an inertial sensor with 10 axes with a triaxial accelerometer, a triaxial gyroscope and a triaxial magnetic sensor, and a barometer for determining local coordinates and the slope of the path taken by the person 1. Moreover, the placement of an inertial sensor with 10 axes on each foot would allow to have a simpler and more precise measurement of the number of steps and of the walking or running pace of the person wearing the portable instrument. The placement of the reference GNSS receiver module on the head is the best position for not being dependent on the movement of the arms or legs.

Figure 4:
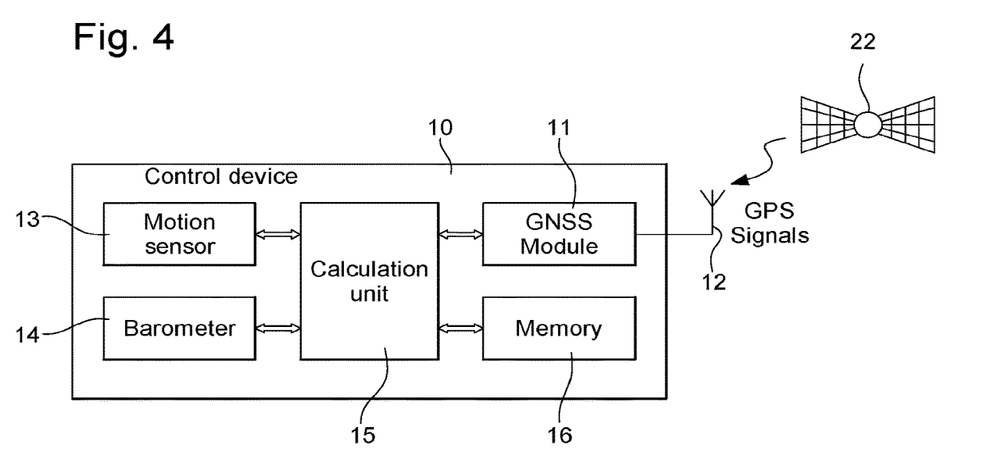
FIG. 4 shows a simplified block diagram of the electronic components of the device for controlling or managing a sports or well-being activity of a person, of the portable instrument according to the invention.

FIG. 4 shows in a more precise manner the various electronic components of the device 10 for controlling or managing a sports or well-being activity of a person of the portable instrument according to the invention. The control device 10 comprises at least one motion sensor 13 connected to a calculation unit 15, which can be a microcontroller clocked by an integrated oscillator not shown. The control device 10 further comprises a GNSS receiver module 11 controlled by the calculation unit 15 to activate or deactivate it. The control device 10 can further comprise a pressure sensor 14, which is a barometer or an altimeter, connected to the calculation unit 15, and at least one memory 16 connected to the calculation unit 15, such as a non-volatile memory 16 capable of memorising various measurements made by the sensor(s) 13, 14 or measurements received by GPS signals from visible satellites 22 by an antenna 12 connected to the GNSS receiver module 11. The control device 10 is generally powered by a battery, not shown, of the portable instrument for its operation.

The calculation unit 15, which is preferably a microcontroller, can comprise in addition to the oscillator, a first counter for determining a time of activation of the GNSS receiver module 11 and a second counter for determining a time of deactivation of the GNSS receiver module 11. A first switching threshold is provided in relation to the first counter and a second switching threshold is provided in relation to the second counter as explained below in reference to the management method in FIG. 5. The activation time and the deactivation time determined in the calculation unit 15 or microcontroller can be defined by a means other than a time counter.

The calculation unit 15, such as the microcontroller, can have memorised a calculation algorithm for the estimation of speed or of pace of the movement of the person. It is also possible according to the invention to memorise the algorithm in the non-volatile memory 16. This algorithm incorporated here by reference was presented by Mr. Abolfazl Soltani et al. in the article entitled "Real-world gait speed estimation using wrist sensor A personalized approach.", and presented in IEEE Journal of Biomedical and Health Informatics (2019). Speed data is thus collected and memorised preferably in the non-volatile memory 16 or a volatile memory to characterise walking or running styles or profiles of a person in daily life by using signals from satellites 22 and signals from the sensors 13, 14. It is thus possible to define a customised model with the goal of only activating the GNSS receiver module 11 during variations in movement or in pressure differing from the variations already known previously and memorised. This allows to reduce the overall consumption of the control device 10 since it is powered by a small battery.

Figure 5:
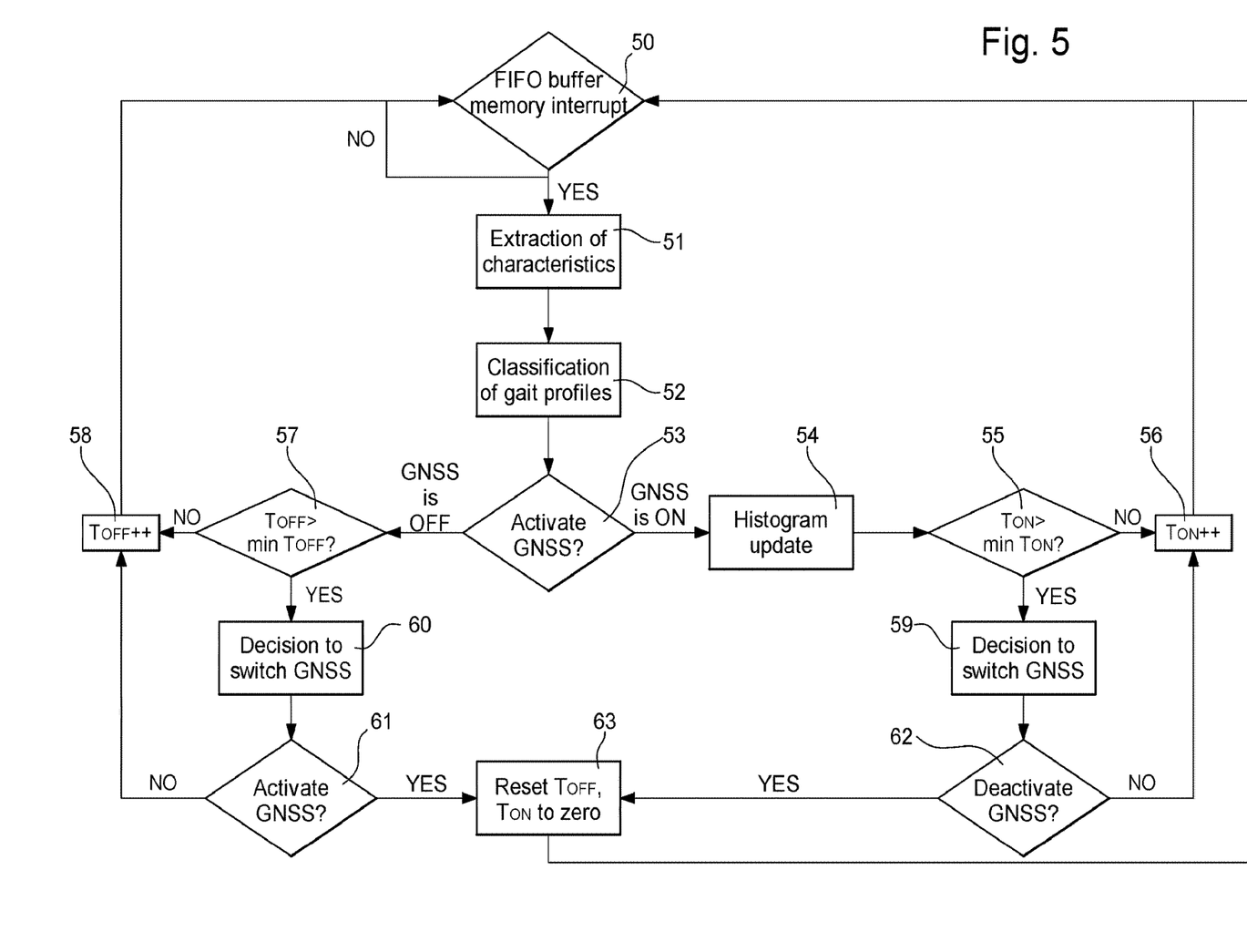
FIG. 5 shows various steps of a method for managing a sports or well-being activity of a person wearing the portable instrument according to the invention.

To better understand the operation of the control device, reference is now made to the method for managing a sports or well-being activity of a person wearing the portable instrument in reference to FIG. 5. As previously indicated according to the present invention, the GNSS proposed strategy is to activate the GNSS receiver module each time that there are new models or profiles of walking or gait of a person in daily life. In FIG. 5 described below, the diagram of the various steps of the GNSS proposed intelligent strategy is shown. In this case, the control device comprises both the motion sensor and the pressure sensor, but in general at least the motion sensor is necessary.

FIFO buffer memory interrupt 50: in this step, the intelligent strategy waits for an interrupt of FIFO buffer memory indicating the presence of new samples after variations in movement of a walking profile not yet memorised. This FIFO buffer memory can be part of the memory for recording speed data and various walking or gait profiles.

Extraction of characteristics 51: The proposed algorithm uses in this example a 3D three-dimensional accelerometer and a barometric pressure sensor to provide a 3D accelerometer signal (A(t)) and a pressure signal (P(t)). The signals are segmented every second using a mobile window of 6 seconds with an overlap of 5 seconds to provide a segmented acceleration (A[n]) and a pressure signal (P[n]), where n indicates the number of the window. Sx [n], Sy [n] and Sz [n] were designated as segmented accelerations along the three axes of measurement of the accelerometer.

With regard to the mobile windows every second, these are mobile windows successive in time each lasting 6 seconds and overlapping by 5 seconds each with a successive window. Thus, the various successive windows are offset by 1 second each time. The clocking of these mobile measurement windows is obtained via the oscillator of the microcontroller and a series of dividers if necessary. With these measurement windows, it is possible to detect the immobility of the person, an incertitude as to the variations in movement or the mobility of the person. The mobility or movement of the person is a parameter necessary but not sufficient for the direct control of the activation of the GNSS receiver module.

When new data from the motion sensor, such as the accelerometer, and from the pressure sensor, such as the barometer, becomes available, two characteristics are extracted according to the equations (1) and (2) below. These characteristics are specially chosen since they allow to group together the various walking models or profiles and their inherent characteristics (for example, fast/slow run, climbing/descent, etc.). A window of 6 seconds with an overlap of 5 seconds with respect to the other successive windows is used for the extraction of the characteristics.

$$F_1[n] = -\frac{\sum_{k=1}^{q}(i-\bar{\tau})\cdot(P^i[n]-\bar{P}[n])}{\sum_{k=1}^{q}(i-\bar{\tau})^2}\cdot F_S \quad (1)$$

$$F_2[n] = \frac{std(S_y[n])}{\frac{1}{q}\sum_{k=1}^{q}|S_y^i[n]-S_y^{i-1}[n]|} \quad (2)$$

where q is the number of samples in the window number n, $F_s$ is the sampling frequency (500 Hz in this case), and $p^i[n]$ is the i-th sample of the pressure vector in the window number n. Moreover, P[n] and i are calculated on the basis of the equations (3) and (4). Std means a standard deviation in which $S_y[n]$ is an acceleration value recorded on the y axis of the sensor. Moreover, $S^i_y[n]$ is the i-th sample of the vector $S_y[n]$.

$$\bar{P}[n] = \frac{1}{q}\sum_{i=1}^{q}P^i[n] \quad (3)$$

$$\bar{\tau} = \frac{1}{q}\sum_{k=1}^{q}i \quad (4)$$

Classification of the walking models or profiles 52: The walking or running model or profile or pace is defined on the basis of a value of F1 and F2 in a histogram table not shown. At this stage, the goal is to decide whether or not the data from the sensors contains new information for the training on the speed model. For this purpose, a histogram table is designed in which each column is in relation to F1 and each row is in relation to F2. The range selected (RF1) and the resolution (dF1) for F1 are defined for example with RF1= [−0.07 to +0.07] and dF1=0.035. Similarly, the range (RF2) and the resolution (dF2) for F2 are defined for example with RF2=[0 to 5] and dF2=0.5. In this case, the space created by <F1, F2> contains 55 cells used to group together each walking model or profile and each cell in the histogram table shows the number of occurrences of the adaptation data in the cell.

Figure 6:
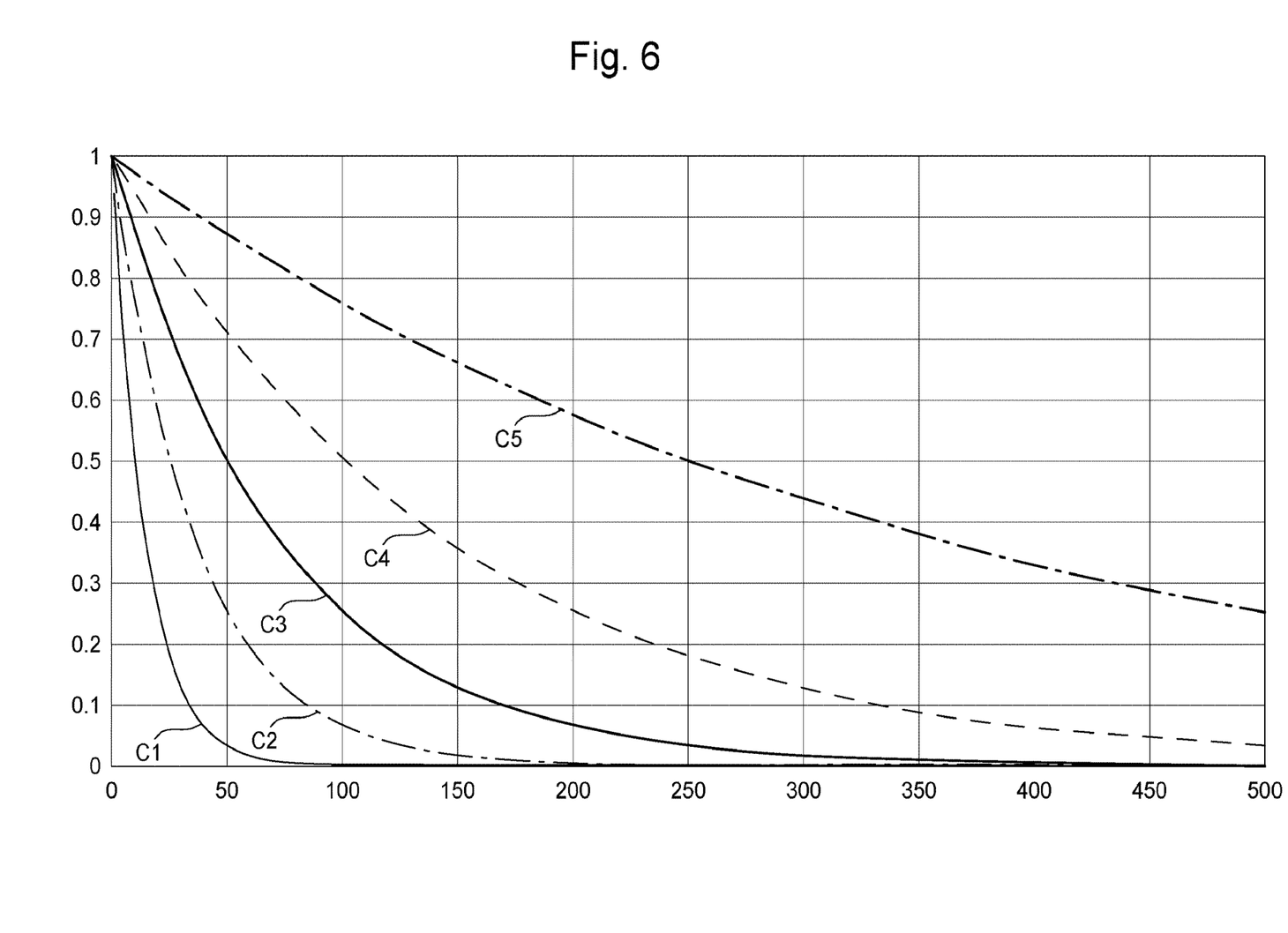
FIG. 6 shows a graph of a reduction in the exponential probabilities for various values of 1 for the starting of the GNSS receiver module of the control device according to the invention.

Finally by using the equation (5), the number of occurrences is translated into a probability value indicating the probability of turning on the GNSS receiver module if a new sample is in the range of one of these cells received from the sensors.

$$P_i = 2^{-\left(\frac{N_i}{\beta}\right)} \quad (5)$$

where $N_i$ is the number of occurrences in each cell and β is the number of times that a situation must appear to reach half of the value of the exponential curve as shown in FIG. 6. The curve c1 is for β equal to 10. The curve c2 is for β equal to 25. The curve c3 is for β equal to 50. The curve c4 is for β equal to 100. The curve c5 is for β equal to 250. At the beginning of the customization, the histogram table is filled with zeros and all the probabilities are equal to 1.

Control of the state of the GNSS 53: in this step, the state of the GNSS receiver module (ON/OFF) is analysed to find the correct execution line in the algorithm.

Histogram update 54: If the GNSS receiver module is already ON, the histogram table containing the number of occurrences of each walking model or profile is updated.

$T_{ON}$>min $T_{ON}$? 55: Each time that the algorithm detects that the GNSS receiver module is ON, the corresponding counter ($T_{ON}$), which is part of the calculation unit or microcontroller, is compared to a threshold (min $T_{ON}$). $T_{ON}$ contains the quantity of consecutive times (expressed in seconds) that the GNSS receiver module is used. The threshold min $T_{ON}$ prevents the GNSS receiver module from changing its state too frequently, since this would cause an unstable behaviour and a greater consumption of current. It is important to consider that the time passed between the moment at which the voltage powers the control device with the GNSS receiver module and the useful measurements of the GNSS receiver module are received can increase by several seconds. In the field of GNSS, this time is known as TTFF ("Time To First Fix") and its value can change greatly according to the initial state of the receiver and the environmental conditions. Consequently, the ON decision for changing the state of the GNSS receiver module will have certain restrictions on the minimum quantity of times that the GNSS receiver module must remain in the same state. These restrictions are governed by the value of the threshold min $T_{ON}$, which can be for example set to 2 minutes, which is the time of activation of the GNSS receiver module.

$T_{ON}$++56: if the threshold condition is not encountered or the GNSS receiver module remains in the same state after the execution of the decision to switch the GNSS receiver module, the counter $T_{ON}$ is incremented.

$T_{OFF}$>min $T_{OFF}$? 57: each time that the algorithm detects that the GNSS receiver module is OFF, the corresponding counter ($T_{OFF}$), which is part of the calculation unit or microcontroller, is compared to a threshold (min $T_{OFF}$). $T_{OFF}$ contains the quantity of consecutive times (expressed in seconds) that the GNSS receiver module is not used. The same restrictions for preventing a change in state of the GNSS receiver module that is too fast are governed by the value of the threshold min $T_{OFF}$, which can be for example set to 10 minutes. This threshold value (deactivation time) can also be defined as greater to take into account already known and memorised walking profiles, and given that at least a shorter activation time of the GNSS receiver module is provided, for example at least 5 times shorter, to be able to at least precisely determine by the activated GNSS receiver module a distance, a position or preferably a speed in an operation of personal calibration of the control device.

$T_{OFF}$++58: if the threshold condition is not exceeded or the GNSS receiver module remains in the same state after the execution of the decision to switch the GNSS receiver module, the counter $T_{OFF}$ is incremented.

Decision to switch the GNSS receiver module 59, 60: on the basis of the probability by using the equation (5), an ON decision is taken whether the change in the state of the GNSS receiver module is executed or not. For example, if the GNSS receiver module is OFF and the probability of switching ON is 75%, a random probability value in the range [0 to 100] is generated for example by using a normal distribution. Later, if the random generated probability is smaller than the probability of switching ON, that is to say 75%, a decision to switch the GNSS receiver module ON is generated. This makes sense since the highest probabilities are expected when new situations appear and thus it is not very probable that the generated random probability has a greater value. Similarly, if the GNSS receiver module is ON and the probability of switching OFF is 75%, the GNSS receiver module would be deactivated (OFF) only if the generated random probability is greater than 75% in this case. Again, this makes sense since low probabilities are expected if the GNSS receiver module is ON since situations are already trained and it is not very probable that the generated random probability has a smaller value.

Activate GNSS (ON)? 61: if the GNSS receiver module is OFF, the decision to switch the GNSS receiver module is controlled to switch it ON.

Deactivate GNSS (OFF)? 62: if the GNSS receiver module is ON, the decision to switch the GNSS receiver module is controlled to switch it OFF.

Set $T_{ON}$, $T_{OFF}$ to zero 63: if the decision to switch the GNSS receiver module is affirmative, the counters $T_{ON}$, $T_{OFF}$ are reset to zero and the algorithm will again start to wait for a new interrupt of the FIFO buffer memory in step 50.

As results for analysing the performance of the intelligent strategy of the GNSS receiver module, the following parameters are focused on:

Level of convergence: The RLS algorithm ("Recursive Least Squares") is used to construct a customised model for estimation of speed. The level of convergence or "learning method" can be studied by examining at least the first element in the diagonal of the covariance matrix of samples. Examination is at this value to study the convergence of the model for estimating speed in comparison to the case in which the samples of the GNSS receiver module are always used.

Use of the GNSS receiver module: each time that the GNSS receiver module is used, a counter is incremented in the microcontroller. This counter is used to control the quantity of uses of the GNSS receiver module required by the GNSS intelligent strategy and study the feasibility and the impact of reduction of this time.

Relative speed error: the relative error for each sample of estimated speed is calculated by using the following expression:

$$Rel.\text{Speed Error} = \left| \frac{\hat{v} - \hat{v}_{ref}}{\hat{v}_{ref}} \right| \cdot 100 \tag{6}$$

where v is the estimated speed and $v_{ref}$ is the GNSS reference speed.

Figure 7:
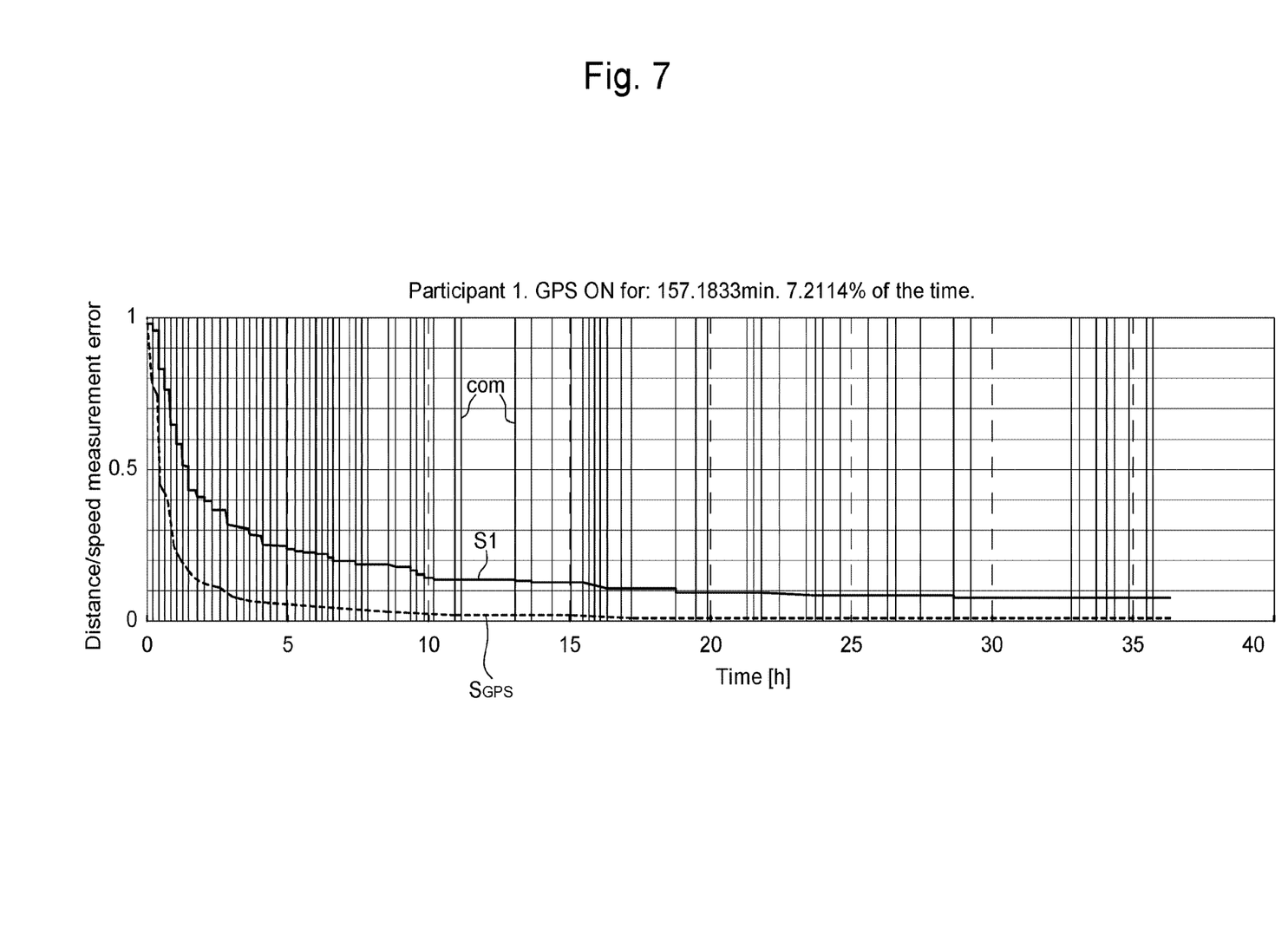
FIG. 7 shows a comparative diagram of the results of the GNSS strategy for a person over time with on the one hand the GPS receiver module permanently activated and on the other hand the GPS receiver module partly subsequent to modifications in walking profile of the person.

FIG. 7 illustrates the results of the application of the GNSS intelligent strategy to one of the participants in a defined database M3. This database contains data coming only from situations currently being executed. The participants do not have any constraints and wear their sensors during their normal running training and their usual trajectory. This database is recorded in the control device worn on the wrist of participant 1 for example.

As visible in FIG. 7, the GNSS receiver module of participant 1 is only used and active for 7.2% of the total time, which is shown over approximately 36 h, that is to say for 157.1833 minutes. The various vertical lines com define the moments of activation of the GNSS receiver module of the present invention. Thus, the distance/speed measurement error of the signal S1 of the GNSS receiver module activated for time periods com is judged to be low and the signal S1 is close to a signal $S_{GPS}$ of a GNSS receiver module, which would be activated continuously for the entire duration of the 36 h. The graph shows more precisely the level of convergence of the customisation (S1), which is expressed by the first element in the diagonal of the covariance matrix of the samples, and which is reasonably close in the case in which the GNSS receiver module is always activated ($S_{GPS}$).

Figure 8:
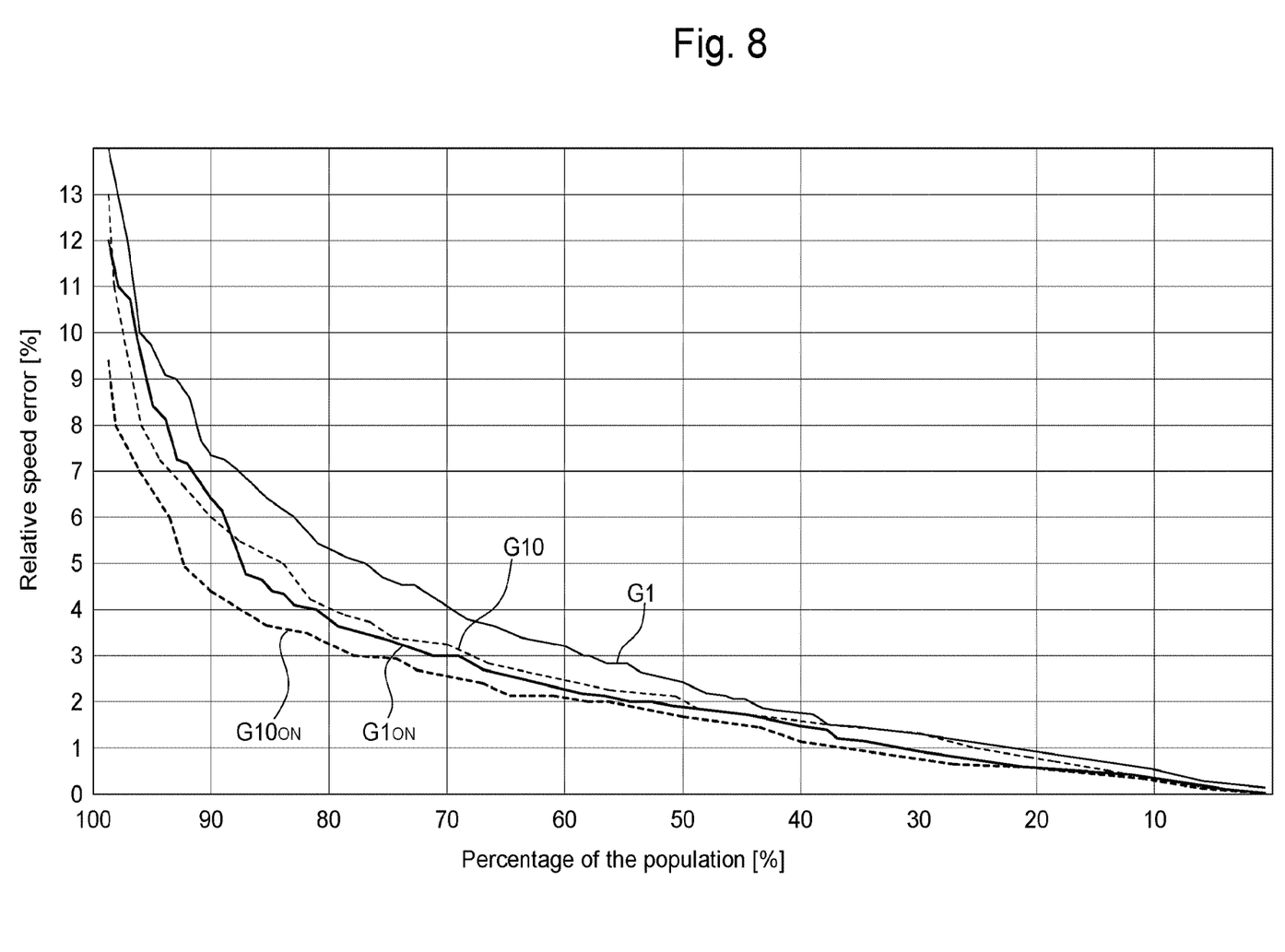
FIG. 8 shows a comparative diagram of the relative error in speed according to the percentage of people using the customised portable instrument with on the one hand the GPS receiver module permanently activated and on the other hand the GPS receiver module partly activated subsequent to modifications in walking profile of the people.

Finally in FIG. 8, the relative error in the estimation of speed for various people (percentage of people) is shown. To compare the performance of the GNSS intelligent strategy to the case in which the GNSS receiver module is used all the time, the relative error is calculated by using the equation (6) for both situations. Indeed, when the GNSS receiver module is always used, the relative error comprises only the tracking error of the RLS algorithm when it is attempted to track the speed reference. Moreover, when the GNSS intelligent strategy is applied, the relative error also comprises the error added by the model for estimating speed when the training method is interrupted. FIG. 8 shows the results for various people when the GNSS intelligent strategy is applied to all the participants in the database M3.

If all the participants are taken into consideration, the relative error is approximately 6.5% when the GNSS receiver module is activated continuously according to the curve G1$_{ON}$. This increases to 7.5% once the GNSS intelligent strategy is applied according to the curve G1 for the GNSS receiver module of the present invention. Moreover, if only the participants, the recordings of which contained for at least 10 hours of data are included, the relative error in the estimation of speed is under 5% according to the curve G10$_{ON}$ when the GNSS receiver module is activated 100% of the time. After the application of the GNSS intelligent strategy, the relative error is close to 6% according to the curve G10 with an activation of the GNSS receiver module below 10%. With this and as shown in the previous Figures, it is clear that the proposed strategy of the present invention can achieve a strong reduction in the use or activation of the GNSS receiver module while maintaining a reasonably low error in the estimation of speed. Moreover, the stability and the level of convergence of the RL model appears to be acceptable in comparison to the case in which the GNSS receiver module is always activated (ON). The duration of the successive activation of the GNSS receiver module can thus be less than 10% of the total time of use of the control device by the calculation algorithm of the calculation unit, that is to say with a maximum time of operation of the GNSS receiver module of approximately 5 hours, said GNSS receiver module no longer being turned on beyond a total time of use of the control device of 50 hours. Thus the control device of the portable instrument can be powered by a small battery, such as a battery of a wristwatch.

Starting from the description that has just been made, a plurality of alternative embodiments of the portable instrument provided with the device for controlling a sports or well-being activity of a person and of the method for starting up the control device are possible without going beyond the context of the invention defined by the following claims. One or more non-volatile memories can be provided and capable of being detached from the control device to equip another portable instrument with all the movement data or customised walking profiles recorded and dedicated to a person. The electric power supply of the portable instrument can be provided by a battery or a solar cell or a thermoelectric generator.

The invention claimed is:

1. A portable instrument, comprising:
a control device configured to control a sports or well-being activity of a person wearing the portable instrument, the control device including calculation circuitry, a pressure sensor and a motion sensor connected to the calculation circuitry, and a GNSS receiver module connected to the calculation circuitry,
wherein the calculation circuitry is configured to
detect, based on signals received from the pressure sensor and the motion sensor, a combination of both pressure data and motion data differing from known movement data stored in a memory of the portable instrument,
activate the GNSS receiver module for an activation time period, only in response to detecting the combination of both pressure data and motion data differing from the known movement data stored in the memory, in order to determine a speed of the person, and
deactivate the GNSS receiver module after the activation time period ends for a deactivation time period greater than the activation time period.

2. The portable instrument according to claim 1, wherein the control device further comprises the memory, which is connected to the calculation circuitry, to store at least speed data and the known movement data corresponding to various walking or running profiles of the person wearing the portable instrument.

3. The portable instrument according to claim 2, wherein the memory stores a recorded calculation algorithm that estimates the speed of the person wearing the portable instrument.

4. The portable instrument according to claim 1, wherein the calculation circuitry is further configured to execute a calculation algorithm to estimate the speed of the person wearing the portable instrument, in order to control the activation or the deactivation of the GNSS receiver module.

5. The portable instrument according to claim 1, wherein the calculation circuitry further comprises a first counter in relation to a first switching threshold to determine the activation time period of the GNSS receiver module and a second counter in relation to a second switching threshold to determine the deactivation time period of the GNSS receiver module.

6. The portable instrument according to claim 1, wherein the pressure sensor is configured to determine an altitude or a slope during a walk or a run on a trajectory or path.

7. The portable instrument according to claim 1, wherein the motion sensor is an accelerometer with three axes of measurement.

8. The portable instrument according to claim 1, wherein the motion sensor is an inertial motion sensor with 9 axes having a triaxial accelerometer, a triaxial gyroscope, and a triaxial magnetic sensor, or an inertial motion sensor with 10 axes having a triaxial accelerometer, a triaxial gyroscope, a triaxial magnetic sensor, and a barometer.

9. The portable instrument according to claim 1, wherein the portable instrument is a wristwatch powered by a battery.

10. The portable instrument of claim 1, wherein the calculation circuitry is further configured to activate the GNSS based on a probability value calculated from a number of times the combination of pressure data and motion data, differing from the known movement data, is detected.

11. A method for managing a sports or well-being activity of a person wearing a portable instrument that includes a control device, the control device including calculation circuitry, a pressure sensor and a motion sensor connected to the calculation circuitry, and a GNSS receiver module connected to the calculation circuitry, wherein the method comprises:
- detecting, based on signals received from the pressure sensor and the motion sensor, a combination of both pressure data and motion data differing from known movement data stored in a memory of the portable instrument,
  - activating the GNSS receiver module for an activation time period, only in response to detecting the combination of both pressure data and motion data differing from the known movement data stored in the memory,
  - determining a speed of the person subsequent to the activation of the GNSS receiver module by reception of GPS signals from satellites, and
  - deactivating the GNSS receiver module after the activation time period for a deactivation time period longer than the activation time period.

12. The management method according to claim 11, further comprising estimating, by the calculation circuitry, the speed of the person wearing the portable instrument using a calculation algorithm in order to control the activation or the deactivation of the GNSS receiver module.

13. The management method according to claim 12,
- wherein the motion sensor is a three-dimensional accelerometer to provide, as the motion data, an accelerometer signal to the calculation circuitry, and the pressure sensor provides, as the pressure data, a pressure signal to the calculation circuitry, and
- wherein the accelerometer signal and the pressure signal are segmented every second using a mobile window of a first duration with an overlap of a second duration with a successive mobile window to provide a segmented acceleration and a segmented pressure signal so as to determine, by the calculation circuitry, whether the combination of the pressure data and the motion data corresponds to a walking model not stored in the memory.

14. The management method according to claim 13, wherein the first duration is equal to 6 seconds and the second duration is equal to 5 seconds according to a clocking of an oscillator of the calculation circuitry.

15. The management method according to claim 13,
- wherein the calculation circuitry comprises a first counter to determine a time of activation of the GNSS receiver module and a second counter to determine a time of deactivation of the GNSS receiver module, wherein after the determination of the walking model or profile, the calculation circuitry is further configured to verify whether the GNSS receiver module is already in an activated state or in a deactivated state,
- wherein when the GNSS receiver module is already in an activated state, the calculation circuitry is further configured to perform a verification of a state of the first counter to determine whether the state of the first counter is below a first minimum threshold, and if so, the first counter is incremented and the previous steps of the method are repeated, and when the state of the first counter is above the first threshold, the calculation circuitry is further configured to verify whether a decision to switch the GNSS receiver module must take place in order to determine whether the GNSS receiver module must be deactivated, and
- wherein when the GNSS receiver module is already in a deactivated state, the calculation circuitry is further configured to perform a verification of a state of the second counter to determine whether the state of the second counter is below a second minimum threshold, and if so, the second counter is incremented and the previous steps of the method are repeated, and when the state of the second counter is above the second threshold, the calculation circuit is further configured to control whether a decision to switch the GNSS receiver module must take place in order to determine whether the GNSS receiver module must be activated.

16. The management method according to claim 15, wherein the activation time period of the GNSS receiver module defined by the first counter is set to 2 minutes, and wherein the deactivation time period of the GNSS receiver module defined by the second counter is greater than 10 minutes and depends on new walking models or profiles detected.

17. The management method according to claim 12, wherein by turning the control device on when the portable instrument is used by the person, a duration of the successive activation of the GNSS receiver module is less than 10% of a total time of use of the control device by the calculation algorithm of the calculation circuitry.

* * * * *